US00PP29711P2

(12) United States Plant Patent
Tuinier

(10) Patent No.: US PP29,711 P2
(45) Date of Patent: Sep. 25, 2018

(54) ***TRADESCANTIA* PLANT NAMED 'NANOUK'**

(50) Latin Name: *Tradescantia albiflora*
Varietal Denomination: Nanouk

(71) Applicant: Wander Durk Tuinier, Krimpen aan den IJssel (NL)

(72) Inventor: Wander Durk Tuinier, Krimpen aan den IJssel (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/530,940

(22) Filed: Mar. 28, 2017

(51) Int. Cl.
*A01H 5/02* (2018.01)

(52) U.S. Cl.
USPC ..... Plt./257

(58) Field of Classification Search
USPC ..... Plt./263.1
See application file for complete search history.

(56) References Cited

PUBLICATIONS

PLUTO Plant Variety Database Feb. 10, 2018.*

* cited by examiner

*Primary Examiner* — Annette H Para
(74) *Attorney, Agent, or Firm* — C. A. Whealy

(57) ABSTRACT

A new and distinct cultivar of *Tradescantia* plant named 'Nanouk', characterized by its compact and upright to broadly spreading plant habit; strong and healthy leaves; light purple, green and greyed green-colored leaves; and good interiorscape performance.

2 Drawing Sheets

Botanical designation: *Tradescantia albiflora.*
Cultivar denomination: 'NANOUK'.

BACKGROUND OF THE INVENTION

The present invention relates to a new and distinct cultivar of *Tradescantia* plant, botanically known as *Tradescantia albiflora* and hereinafter referred to by the name 'Nanouk'.

The new *Tradescantia* plant is a product of a planned breeding program conducted by the Inventor in Sappemeer, The Netherlands. The objective of the breeding program was to create new compact *Tradescantia* plants with attractive flower coloration and good performance.

The new *Tradescantia* plant originated from a cross-pollination in 2012 in Sappemeer, The Netherlands, of two unnamed seedling selections of *Tradescantia albiflora*, not patented. The new *Tradescantia* plant was discovered and selected by the Inventor as a single flowering plant from within the progeny of the stated cross-pollination in a controlled environment in Sappemeer, The Netherlands.

Asexual reproduction of the new *Tradescantia* plant by terminal cuttings in a controlled environment in Sappemeer, The Netherlands since March, 2013 has shown that the unique features of this new *Tradescantia* plant are stable and reproduced true to type in successive generations.

SUMMARY OF THE INVENTION

Plants of the new *Tradescantia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'Nanouk'.

These characteristics in combination distinguish 'Nanouk' as a new and distinct *Tradescantia* plant:

1. Compact and upright to broadly spreading plant habit.
2. Strong and healthy leaves.
3. Light purple, green and greyed green-colored leaves.
4. Good interiorscape performance.

Plants of the new *Tradescantia* and the parent selections differ primarily in leaf color as plants of the parent selections have white and green-colored leaves.

Plants of the new *Tradescantia* can be compared to plants of the *Tradescantia spathacea* 'Tricolor', not patented. In side-by-side comparisons, plants of the new *Tradescantia* and 'Tricolor' differ primarily in leaf shape as plants of new *Tradescantia* have shorter and more rounded leaves than plants of 'Tricolor'.

Plants of the new *Tradescantia* can also be compared to plants of the *Tradescantia albiflora* 'Albovittata', not patented. In side-by-side comparisons, plants of the new *Tradescantia* and 'Albovittata' differ primarily in leaf color as plants of 'Albovittata' have white and green-colored leaves.

BRIEF DESCRIPTION OF THE PHOTOGRAPHS

The accompanying colored photographs illustrate the overall appearance of the new *Tradescantia* plant showing the colors as true as it is reasonably possible to obtain in colored reproductions of this type. Colors in the photographs may differ slightly from the color values cited in the detailed botanical description which accurately describe the colors of the new *Tradescantia* plant.

The photograph on the first sheet comprises a side perspective view of a typical plant of 'Nanouk' grown in a container.

The photograph on the second sheet is a close-up view of a typical plant of 'Nanouk'.

DETAILED BOTANICAL DESCRIPTION

The aforementioned photographs and following observations, measurements and values describe plants grown in 12-cm containers during the winter in a glass-covered greenhouse in Sappemeer, The Netherlands and under cultural practices typical of commercial *Tradescantia* production. During the production of the plants, day temperatures ranged from 20° C. to 25° C. and night temperatures ranged from 18° C. to 20° C. Plants were 18 weeks old when the photographs and description were taken. In the following description, color references are made to The Royal Horticultural Society Colour Chart, 2015 Edition, except where general terms of ordinary dictionary significance are used.

Botanical classification: *Tradescantia albiflora* 'Nanouk'.

Parentage:

*Female, or seed, parent*.—Unnamed selection of *Tradescantia albiflora*, not patented.

*Male, or pollen, parent*.—Unnamed selection of *Tradescantia albiflora*, not patented.

Propagation:

*Type*.—By terminal cuttings.

*Time to initiate roots, summer*.—About one week at temperatures about 21° C.

*Time to initiate roots, winter*.—About two weeks at temperatures about 18° C.

*Time to produce a rooted young plant, summer*.—About three weeks at temperatures about 21° C.

*Time to produce a rooted young plant, winter*.—About four weeks at temperatures about 18° C.

*Root description*.—Thick; typically whitish in color.

*Rooting habit*.—Freely branching; medium in density.

Plant description:

*Plant form and growth habit*.—Herbaceous perennial; compact and upright to broadly spreading plant habit; flattened globular in overall shape; low vigor to moderately vigorous growth habit; good interiorscape performance with plants maintaining good quality for one to two years.

*Plant height*.—About 8.9 cm.

*Plant width* (*spread*).—About 8.6 cm.

*Basal branches*.—Length: About 4.9 cm. Diameter: About 5 mm. Internode length: About 1.6 cm. Strength: Moderately strong. Aspect: Variable, between 30° and 80° from vertical. Texture and luster: Smooth, glabrous; glossy. Color, developing: Close to 148A. Color, developed: Close to darker than 148A; axially-striped, close to N77D; at the internodes, close to N77C to N77D.

Leaf description:

*Arrangement*.—Distichous; leaves simple and sessile.

*Length*.—About 4.2 cm.

*Width*.—About 2.8 cm.

*Shape*.—Ovate to elliptic.

*Apex*.—Acute.

*Base*.—Cuneate, sheathing.

*Margin*.—Entire.

*Aspect*.—Slightly concave.

*Texture and luster, upper and lower surfaces*.—Smooth, glabrous; at the base, sparsely pubescent; slightly glossy.

*Venation pattern*.—Parallel.

*Color*.—Developing leaves, upper surface: Close to N75A to N75D; variable stripes, close to 147A. Developing leaves, lower surface: Close to NN78A; variable stripes, close to N186B. Fully expanded leaves, upper surface: Close to 75B and N75D; variable stripes, close to NN137A, 147A and 189A. Fully expanded leaves, lower surface: Close to NN78A; variable stripes, close to 79A and N186B.

Flower description: To date, flower initiation and development have not been observed on plants of the new *Tradescantia*.

*Seeds and fruits*.—To date, seed and fruit development have not been observed on plants of the new *Tradescantia*.

Pathogen & pest resistance: Plants of the new *Tradescantia* have not been noted to be resistant to pathogens and pests common to *Tradescantia* plants.

Temperature performance: Plants of the new *Tradescantia* have been observed to tolerate temperatures ranging from 12° C. to 40° C. and to be suitable for USDA Hardiness Zones 10 to 12.

It is claimed:

1. A new and distinct *Tradescantia* plant named 'Nanouk' as illustrated and described.

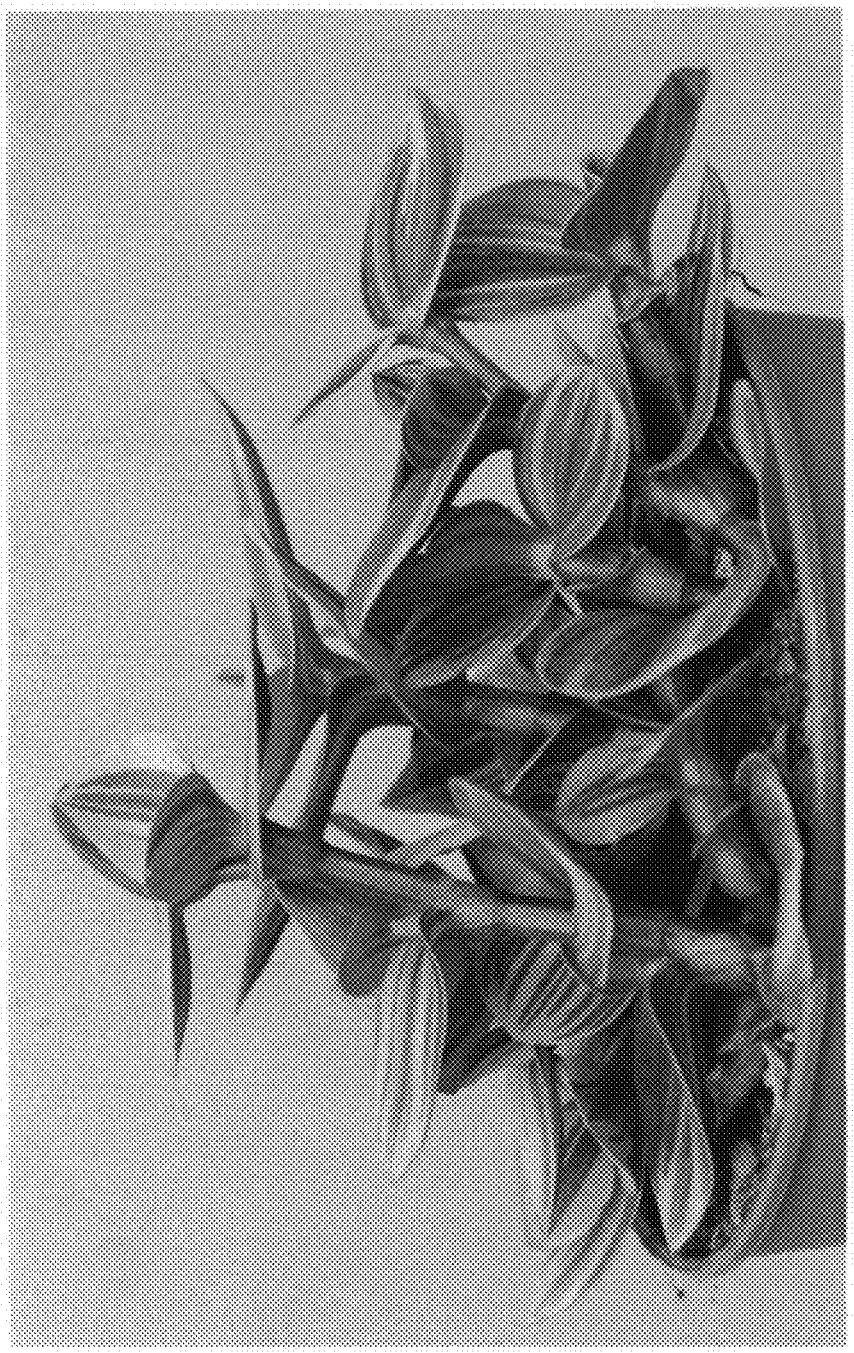

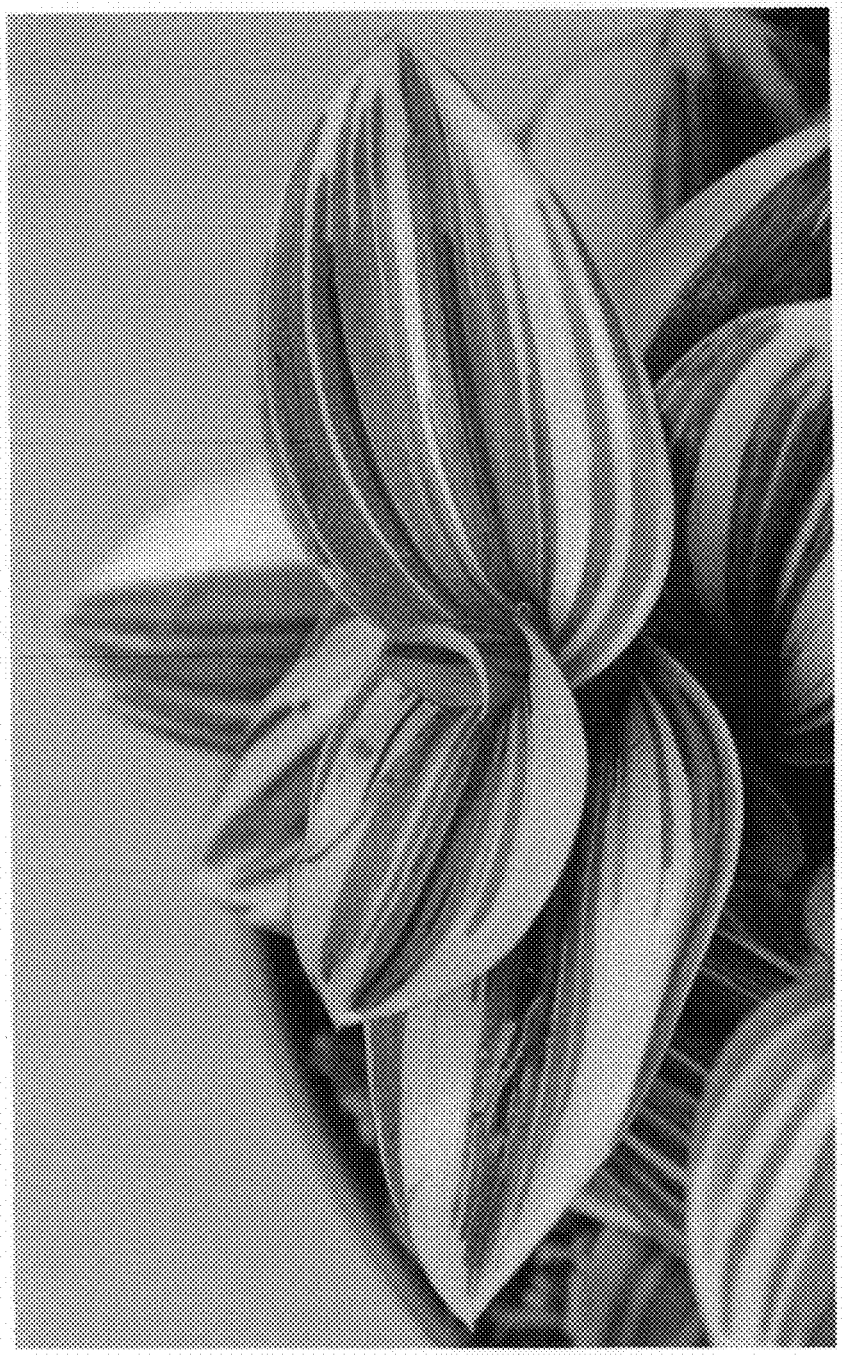

* * * * *